United States Patent [19]

Palfreyman et al.

[11] Patent Number: 5,547,991
[45] Date of Patent: Aug. 20, 1996

[54] NMDA ANTAGONISM METHOD

[75] Inventors: Michael G. Palfreyman, Cincinnati; Ian A. McDonald, Loveland; Francesco G. Salituro, Fairfield, all of Ohio; Robert Schwarcz, Baltimore, Md.

[73] Assignee: Merrell Pharmaceuticals Inc., Cincinnati, Ohio

[21] Appl. No.: 502,980

[22] Filed: Jul. 17, 1995

Related U.S. Application Data

[62] Division of Ser. No. 165,144, Dec. 10, 1993, Pat. No. 5,484,814, which is a division of Ser. No. 57,195, May 3, 1993, abandoned, which is a continuation of Ser. No. 827,188, Feb. 3, 1992, abandoned, which is a continuation-in-part of Ser. No. 662,670, Feb. 28, 1991, abandoned.

[51] Int. Cl.$^6$ .................................................. A61K 31/195
[52] U.S. Cl. .................................................. 514/564
[58] Field of Search .................................................. 514/564

[56] References Cited

U.S. PATENT DOCUMENTS

| | | | |
|---|---|---|---|
| 3,445,479 | 5/1969 | Hydorn | 260/326.16 |
| 4,140,697 | 2/1979 | Batcho et al. | |

FOREIGN PATENT DOCUMENTS

| | | |
|---|---|---|
| 0421946 | 9/1990 | European Pat. Off. |
| WO8603489 | 12/1985 | WIPO |
| WO8809789 | 12/1988 | WIPO |

OTHER PUBLICATIONS

*The Journal of Neuroscience*, Sep. 1990, 10(9):2965–297: Cerebral Synthesis and Release of Kynurenic Acid: an Endogenous Antagonist of Excitatory Amino Acid Receptors.
*Society For Neuroscience Abstracts*, vol. 17, 1991; 315.3; Systemic Loading with Kynurenine and Probenecid Markedly increases Striatal Kynurenic Acid Levels as Measured by In Vivo Microialysis, Miller, et al.
Chemical Abstracts 112(7):52836c; Uptake of kynurenine into rat brain slices, Speciale, et al. (1990).
Chemical Abstracts 76(25):150339a:Enzymic studies of the biosnythesis of 5–hydroxyl–L–kynurenine in the rat small intestine, Konishi (1972).
Chemical Abstracts 75 (3): 17141t; Pyrrole ring cleavaging enzyme of 5–hydroxytryptophan, konishi, et al. (1971).
Chemical Abstracts 69(9):33829e; Formation of 5–hydroxy-–L–kynurenine from L–kynurenine by hen liver microsomes; Kido, et al. (1968).
Chemical Abstracts 72(3)9673r; Influence of androgens on tryptophan metabolism in man, McGinty, et al. (1970).
Chemical Abstracts 74(21):107987g; Gas chromatographic analysis of tryptophan metabolites, Noguchi et al. (1971).
Chemical Abstracts 72(21):107236v; 5–Hydroxykynurenine decarboxylase in rat intestine, Noguchi, et al (1970).
Chemical Abstracts 67(21):96860n; (1967) Metabolism of tryptophan, Griggio et al.
Chemical Abstracts 111 (24):219114j; Sunscreens and skin-–lightening cosmetics containing kynurenines; Narutomi, et al. (1989).
Chemical Abstracts 92(5):36767u; The Mechanism of Kynurenine hydrolysis catalyzed by kynureninase, Tanizawa, et al. (1980).
Chemical Abstracts 97(15):125986K; Halogenoanthrany-loylalanines as sweeteners; Tanabe (1982).
Chemical Abstracts 93(25):239866u; An intensely sweet analog of kynurenine; Kawashima, et al. (1980).
Chemical Abstracts, 109:48451u (1988).
Chemical Abstracts, 106:207831z (1987).
Chemical Abstracts, 95:55548b (1981).
Chemical Abstract, 106:78724r (1987).
Chemical Abstracts, 72:30438c (1970).
Chemical Abstracts, 83:131913m (1975).
Chemical Abstracts, 83:114922w (1975).
Chemical Abstracts, 96: 11515w (1982).
Beilsteins Handbuch Org. Chem. Syst. EII Nr. 3436, p. 420 (1951).
Beilsteins Handbuch, Org. Chem. EIII/IV Syst. Nr. 3436, p. 6,809 and 6817 (1980).
*Kynurenine metabolites of tryptophan: Implications for neurologic diseases;* Freese, et al. 40 Neurology 691–695; Apr. 1990.
10–Microbia Biochem, vol. 112, 1990, Abstract No. 135860g.

*Primary Examiner*—David B. Springer
*Attorney, Agent, or Firm*—J. Michael Dixon

[57] ABSTRACT

The present invention is directed to a class of 4,6-disubstituted tryptophan derivatives, 4,6-disubstituted kynurenines, their use as NMDA antagonists and to pharmaceutical compositions containing these compounds.

10 Claims, No Drawings

NMDA ANTAGONISM METHOD

This is a divisional, of application Ser. No. 08/165,144, filed Dec. 10, 1993, now U.S. Pat. No. 5,484,814, which is a divisional of application Ser. No. 08/057,195 filed May 3, 1993, now abandoned, which was a continuation of Ser. No. 07/827,188, filed Feb. 3, 1992, now abandoned, which was a continuation in part of Ser. No. 07/662,670, filed Feb. 28, 1991, now abandoned, herein incorporated by reference.

The present invention is directed to a new class of excitatory amino acid antagonists, their use in the treatment of disease states such as epilepsy, anxiety, stroke, and to pharmaceutical or diagnostic compositions containing these excitatory amino acid antagonists. A further aspect of this invention is directed to the discovery of a new use for a group of known 6-halo-tryptophan and 4-halo-kyurenine derivatives.

In accordance with the present invention, it has been discovered that the following class of tryptophan derivatives are excitatory amino acid antagonists:

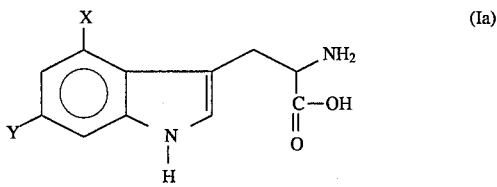

(Ia)

in which X and Y are each independently selected from the group consisting of Cl, Br, F, $CH_3$, and $CH_2CH_3$; or a pharmaceutically acceptable salt thereof.

It has also been discovered that the following kynurenine derivatives are excitatory amino acid antagonists:

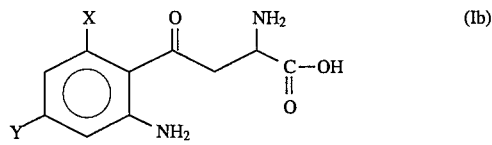

(Ib)

in which X and Y are each independently selected from the group consisting of Cl, Br, F, $CH_3$, and $CH_2CH_3$; or a pharmaceutically acceptable salt thereof.

Additionally, it has been discovered that the following known compounds are excitatory amino acid antagonists:

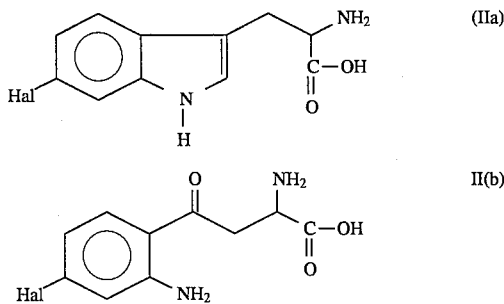

(IIa)

(IIb)

in which Hal is represented by a halogen atom, or a pharmaceutically acceptable salt thereof.

As used in this application:
a) the term "halogen" refers to a fluorine, chlorine, or bromine atom;
b) the term "pharmaceutically acceptable addition salts" refers to either an acid addition or a basic addition salt.

The compounds of Formula Ia, Ib, IIa, and IIb can exist as either pharmaceutically acceptable acid addition salts or as pharmaceutically acceptable basic addition salts. These compounds may also exist as zwitterions.

The expression "pharmaceutically acceptable acid addition salts" is intended to apply to any non-toxic organic or inorganic acid addition salt of the base compounds represented by Formula Ia, Ib, IIa, IIb or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-totuenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by Formula Ia, Ib, IIa, IIb or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

All of the compounds of Formula Ia, Ib, IIa, and IIb contain a chiral center and thus can exist as optical isomers. Any reference to these compounds or their intermediates should be construed as referring to either a racemic mixture or an individual optical isomer. The specific optical isomers can be separated and recovered by techniques known in the art such as chromatography on chiral stationary phases or resolution via chiral salt formation and subsequent separation by selective crystallization. Alternatively utilization of a specific optical isomer as the starting material will produce the corresponding isomer as the final product.

The compounds of Formula Ia are substituted at the 4 and 6 positions as is indicated by the X and Y substituents. X and Y can be represented by the same substituent or by differing substituents. The compounds of Formula Ib are substituted at positions 4 and 6 as is indicated by the X and Y substituents. X and Y can be represented by the same substituents or differing substituents.

Examples of compounds encompassed by Formula Ia include:
  4-Bromo-6-fluorotryptophan;
  4-Bromo-6-chlorotryptophan;
  4-Ethyl-6-bromotryptophan;
  4,6-Dibromotryptophan;
  4,6-Dichlorotryptophan;

Examples of compounds encompassed by Formula Ib include:
  4,6-Dichlorokynurenine;
  4-fluoro-6-Bromo-kynurenine;
  4-chloro-6-bromokynurenine;
  4,6-Dibromo-kynurenine;
  6-Ethyl-4-bromokynurenine;

Examples of compounds encompassed by Formula IIa include:

6-chloro-tryptophan;

6-fluoro-tryptophan.

Examples of compounds encompassed by Formula IIb include:

4-chloro-kynurenine;

4-fluoro-kyurenine.

It is preferred for X and Y to each be represented by a halogen atom in either the tryptophans of Ia or the Kynurenines of Ib.

The compounds of Formula Ia may be prepared using techniques and procedures well known and appreciated by one of ordinary skill in the art. A general synthetic procedure for preparing these compounds is set forth in Scheme A. In Scheme A, all substituents unless otherwise indicated are as previously defined.

Scheme A

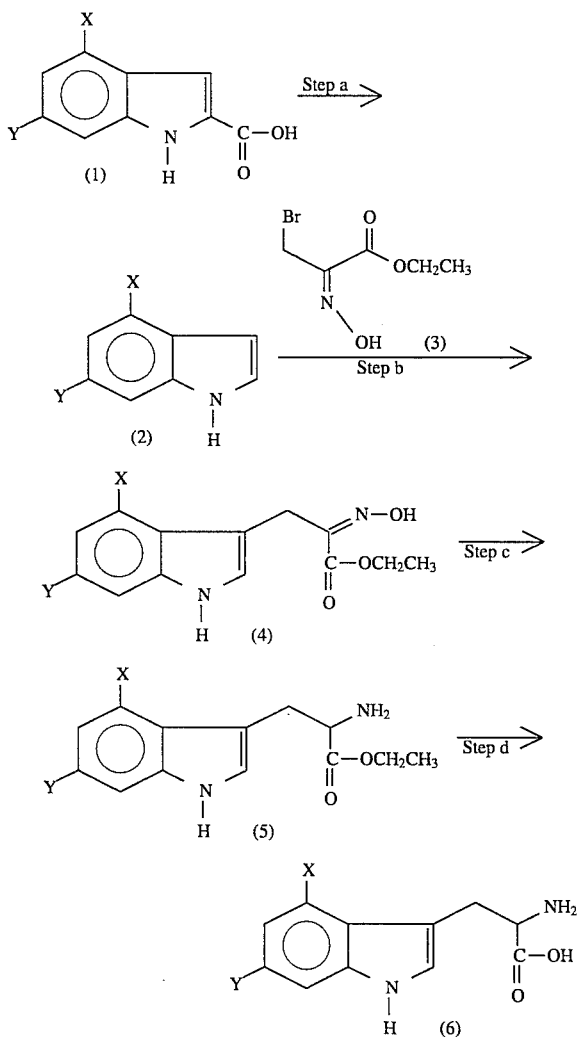

Scheme A provides a general synthetic scheme for preparing compounds of Formula Ia.

In step a, the appropriate 4,6-substituted indole-2-carboxylic acid of structure (1) is decarboxylated to give the corresponding 4,6-substituted indole of structure (2).

For example, the appropriate 4,6-substituted indole-2-carboxylic acid of structure (1) is contacted with a catalytic amount of copper. The reactants are typically contacted in a suitable organic solvent such as quinoline. The reactants are typically stirred together for a period of time ranging from 1–5 hours and at a temperature range of from 200°–220° C. The 4,6-substituted indole of structure (2) is recovered from the reaction zone by extractive methods as is known in the art. It may be purified by silica gel chromatography.

In step b, the appropriate 4,6-substituted indole of structure (2) is alkylated with ethyl 3-bromo-2-hydroxyiminopropanoate (3) to give the ethyl 2-(hydroxyimino)-3-(4,6-substituted-3-indolyl)propanoate of structure (4).

For example, the appropriate 4,6-substituted indole of structure (2) is contacted with a molar equivalent of ethyl 3-bromo-2-hydroxyiminopropanoate (3) and a molar excess of a suitable base such as potassium carbonate. The reactants are typically contacted in a suitable organic solvent such as methylene chloride. The reactants are typically stirred at room temperature together for a period of time ranging from 10–50 hours. The ethyl 2-(hydroxyimino)-3-(4,6-substituted-3-indolyl)propanoate of structure (4) is recovered from the reaction zone by extractive methods as is known in the art. It may be purified by silica gel chromatography.

In step c, hydroxyimino functionality of the appropriate ethyl 2-(hydroxyimino)-3-(4,6-substituted-3-indolyl)propanoate of structure (4) is reduced to give the 4,6-substituted tryptophan ethyl ester of structure (5).

For example, the appropriate ethyl 2-(hydroxyimino)-3-(4,6-substituted-3-indolyl)propanoate of structure (4) is contacted with a molar excess of zinc. The reactants are typically contacted in a suitable acidic solvent, such as acetic acid. The reactants are typically stirred together at room temperature for a period of time ranging from 10–100 hours. The 4,6-substituted tryptophan ethyl ester of structure (5) is recovered from the reaction zone by extractive methods as is known in the art. It may be purified by silica gel chromatography.

In step d, the ethyl ester functionality of the appropriate 4,6-substituted tryptophan ethyl ester of structure (5) is removed to give the corresponding 4,6-substituted tryptophan of structure (6).

In order to facilitate the purification of the tryptophan of structure (6), the amino functionality of the appropriate 4,6-substituted tryptophan ethyl ester of structure (5) is first protected as its carbobenzyloxy derivative.

For example, the appropriate 4,6-substituted tryptophan ethyl ester of structure (5) is contacted with molar equivalent of benzyl chloroformate and a slight molar excess of triethylamine. The reactants are typically contacted in a suitable organic solvent such as methylene chloride. The reactants are typically stirred together at room temperature for a period of time ranging from 5–24 hours. The intermediate 4,6-substituted tryptophan-carbobenzyloxy ethyl ester is recovered from the reaction zone by extractive methods as is known in the art. It may be purified by silica gel chromatography.

The ethyl ester functionality of the appropriate intermediate 4,6-substituted tryptophan-carbobenzyloxy ethyl ester is then removed to give the intermediate 4,6-substituted tryptophan-carbobenzyloxy.

For example, the appropriate intermediate 4,6-substituted tryptophan-carbobenzyloxy ethyl ester is contacted with a molar excess of a suitable base such as lithium hydroxide. The reactants are typically contacted in a suitable solvent mixture such as tetrahydrofuran/water. The reactants are typically stirred together at room temperature for a period of time ranging from 1–5 hours. The intermediate 4,6-substituted tryptophan-carbobenzyloxy is recovered from the reaction zone by extractive methods as is known in the art. It may be purified by silica gel chromatography.

The carbobenzyloxy functionality of the appropriate intermediate 4,6-substituted tryptophan-carbobenzyloxy-carbonyl is then removed to give the 4,6-substituted tryptophan of structure (6).

For example, the appropriate intermediate 4,6-substituted tryptophan-carbobenzyloxy is contacted with a molar excess of trimethylsilyl iodide. The reactants are typically contacted in a suitable organic solvent such as chloroform. The reactants are typically stirred together at room temperature for a period of time ranging from 1–5 hours. The 4,6-substituted tryptophan of structure (6) is recovered from the reaction zone by extractive methods as is known in the art.

Starting materials for use in Scheme A are readily available to one of ordinary skill in the art. For example, certain 4,6-substituted indole-2-carboxylic acids are described in *J. Med. Chem.* 33 2944–46 1990.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "µL" refers to microliters; "µg" refers to micrograms; and "µM" refers to micromolar.

EXAMPLE 1

DL-4,6-Dichlorotryptophan

Step a: 4,6-Dichloroindole

Dissolve 4,6-dichloro-indole-2-carboxylic acid (1.0 g, 4.35 mmol) in quinoline (25 mL). Add copper powder (100 mg) and heat to 220° C. for 3 hours. Pour the resulting black solution into cold concentrated hydrochloric acid (300 mL) and extract into ethyl ether (500 mL). Filter, wash with 1M hydrochloric acid (2×200 mL), water (100 mL) and dry ($MgSO_4$). Evaporate the solvent in vacuo to give a brown oil (0.76 g). Purify by silica gel chromatography (17% ethyl acetate/hexane) to give the title compound as an amber oil (0.66 g, 81%).

$^1$H NMR ($CDCl_3$/TMS): 6.56–6.59 ppm (1H, m), 7.10–7.13 ppm (2H, m), 7.16–7.18 ppm (1H, m). $^{13}$C NMR ($CDCl_3$), ppm: 101.48, 110.16, 120.24, 125.77, 125.94, 126.54, 122.79, 106.54.

Step b: Ethyl 2-(hydroxyimino)-3-(4,6-dichloro-3-indolyl)propanoate

Mix 4,6-dichloroindole (5.90 g, 31.72 mmol), potassium carbonate (1.81 g, 47.6 mmol) and anhydrous methylene chloride (200 mL). Stir and add a solution of ethyl 3-bromo-2-hydroxyiminopropanoate (7.00 g, 33.31 mmol) in methylene chloride (75 mL). Stir under a nitrogen atmosphere for 48 hours. Take the solution up in methylene chloride (100 mL) and wash with water (300 mL), saturated sodium hydrogen carbonate (200 mL) and brine (100 mL). Dry ($MgSO_4$) and evaporate the solvent in vacuo to give a tan solid. Purify by silica gel chromatography (1 to 3% acetone in chloroform) to give the title compound as a yellow solid (7.00 g, 99% based on consumed starting material). Recrystallize (diethyl ether/hexane) to give the title compound as white crystals (4.0 g, 56%); mp 175°–176° C.

$^1$H NMR (DMSO-$d_6$/TMS): 1.19 ppm (3H, t), 4.15 ppm (2H, q), 4.15 ppm (2H, s), 6.95 ppm (1H, s), 7.10 ppm (1H, d), 7.40 ppm (1H, d), 11.3 ppm (1H, bs), 12.35 (1H, s).

Anal. Calcd for $C_{13}H_{12}Cl_2N_2O_3$: C 49.54; H, 3.84; N, 8.89; Found: C, 49.30; H, 3.78; N, 8.62.

Step c: DL-4,6-Dichlorotryptophan ethyl ester

Dissolve ethyl 2-(hydroxyimino)-3-(4,6-dichloro-3-indolyl)propanoate (1.10 g, 3.65 mmol) in acetic acid (200 mL) and add activated zinc dust (1.25 g, 19.2 mmol). Stir at room temperature for 72 hours. Evaporate the acetic acid in vacuo to give a white oil. Take the white oil up in ethyl acetate (200 mL) and treat with saturated sodium hydrogen carbonate (500 mL). Filter the resulting white precipitate and separate the organic phase. Wash with saturated sodium hydrogen carbonate (100 mL) and brine (100 mL). Dry ($MgSO_4$) and evaporate the solvent in vacuo to give the title compound as an amber oil (1.02 g, 98%).

$^1$H NMR ($CDCl_3$/TMS): 1.25 pppm (3H, t), 1.9 ppm (2H, bs), 3.05 ppm (1H, m), 3.55 ppm (1H, m), 3.9 ppm (1H, m), 4.15 ppm (2H, q), 7.05 ppm (1H, s), 7.05 ppm (1H, d), 7.19 ppm (1H, d), 8.70 ppm (1H, bs).

Step d: DL-4,6-Dichlorotryptophan

Mix DL-4,6-dichlorotryptophan ethyl ester (2.37 g, 7.90 mmol) and pyridine (100 mL). Add benzyl chloroformate (2.89 g, 16.98 mmol) and stir for 12 hours. Dilute with ethyl acetate, wash with 1M hydrochloric acid (2×200 mL) and brine (2×200 mL). Dry ($MgSO_4$) and evaporate the solvent in vacuo to give a yellow oil (3.24 g). Purify by recrystallization (hexane/ethyl acetate) to give DL-4,6-dichlorotryptophan-benzyloxycarbonyl ethyl ester as white needles (2.37 g, 70%); mp 151°–153° C.

$^1$H NMR ($CDCl_3$/TMS): 1.20 ppm (3H, t), 3.35 ppm (1H, m), 3.60 ppm (1H, dd), 4.15 ppm (2H, q), 4.75 ppm (1H, m), 5.00 ppm (2H, s), 5.35 ppm (1H, d), 7.00 ppm (1H, s), 7.13 ppm (1H, d), 7.3 ppm (6H, m), 8.10 ppm (1H, bs).

Anal. Calcd for $C_{21}H_{20}Cl_2N_2O_4$: C, 57.94; H, 4.63; N, 6.44; Found: C, 57.58; N, 4.33; N,6.35.

Mix DL-4,6-dichlorotryptophan-benzyloxycarbonyl ethyl ester (2.10 g, 4.88 mmol) in 1:1 tetrahydrofuran/water (100 mL) and add lithium hydroxide monohydrate (615 mg, 14.6 mmol). Stir at room temperature for 2 hours. Pour into 1M hydrochloric acid (200 mL) and extract with ethyl acetate (200 mL). Dry ($MgSO_4$) and evaporate the solvent in vacuo to give DL-4,6-dichlorotryptophan-benzyloxycarbonyl as an amber gum (1.90 mg, 100%).

$^1$H NMR ($CDCl_3$/TMS): 3.35 ppm (1H, m), 3.65 ppm (1H, dd), 4.75 ppm (1H, m), 5.05 ppm (2H, s), 5.45 ppm (1H, s), 7.00 ppm (1H, s), 7.13 ppm (1H, d), 7.3 ppm (6H, m), 8.35 ppm (1H, bs).

Dissolve DL-4,6-dichlorotryptophan-benzyloxycarbonyl (1.99 g, 4.88 mmol) in chloroform (100 mL) and add trimethylsilyl iodide (4.88 g, 24.4 mmol). Stir at room temperature for 0.5 hours, quench with methanol and evaporate the solvent in vacuo to give a violet oil. Take up the residue in isopropanol (200 mL) containing a small amount of DL-dithiothreitol. Neutralize the resulting pale yellow solution with propylene oxide (1.45 g, 25 mmol) to give a white solid (1.15 g, 86%).

FTIR (KBr) $cm^{-1}$: 3418 (NH), 3033 (COOH), 1616 (C=O), 1586–1479 (Aromatic C=C). $^1$H NMR ($CDCl_3$/TFA/TMS): 3.25 ppm (1H, dd), 4.13 ppm (1H, dd), 4.8 ppm (1H, m), 7.15 ppm (1H, d), 7.2 ppm (1H, s), 7.35 ppm (1H, d), 8.5 ppm (1H, bs). $^{13}$C NMR ($CDCl_3$/TFA) ppm: 27.2, 55.4, 106.5, 110.9. 121.7, 122.0, 125.5, 126.9, 129.5, 138.2, 170.25. MS (m/z): 273 (M+, 100%), 255, 237, 227.

Anal. Calcd for $C_{11}H_9Cl_2N_2O_2$.⅕$H_2O$: C, 47.92; H, 3.44; N, 10.16; Found: C, 47.96; H, 3.84; N, 9.97.

EXAMPLE 2

DL-4,6-Dibromotryptophan

Step a: 4,6-Dibromoindole

Dissolve 5,7-dibromo-indole-2-carboxylic acid (1.39 g, 4.35 mmol) in quinoline (25 mL). Add copper powder (100 mg) and heat to 220° C. for 3 hours. Pour the resulting black solution into cold concentrated hydrochloric acid (300 mL) and extract into ethyl ether (500 mL). Filter, wash with 1M hydrochloric acid (2×200 mL), water (100 mL) and dry (MgSO$_4$). Evaporate the solvent in vacuo to give the title compound.

Step b: Ethyl 2-(hydroxyimino)-3-(4,6-dibromo-3-indolyl)propanoate

Mix 4,6-dibromoindole (2.09 g, 7.58 mmol), potassium carbonate (1.57 g, 11.4 mmol) and anhydrous methylene chloride (30 mL). Stir and add a solution of ethyl 3-bromo-2-hydroxyiminopropanoate (1.59 g, 7.58 mmol) in methylene chloride (20 mL). Stir under a nitrogen atmosphere for 48 hours. Take the solution up in ethyl acetate and wash with water (100 mL), saturated sodium hydrogen carbonate (100 mL) and brine (100 mL). Dry (MgSO$_4$) and evaporate the solvent in in vacuo and purify by silica gel chromatography to give the title compound.

Step c: DL-4,6-Dibromotryptophan ethyl ester

Dissolve ethyl 2-(hydroxyimino)-3-(4,6-dibromo-3-indolyl)propanoate (1.47 g, 3.65 mmol) in acetic acid (200 mL) and add activated zinc dust (1.25 g, 19.2 mmol). Stir at room temperature for 72 hours. Evaporate the acetic acid in vacuo and take up in ethyl acetate (200 mL). Treat with saturated sodium hydrogen carbonate (500 mL). Filter the resulting white precipitate and separate the organic phase. Wash with saturated sodium hydrogen carbonate (100 mL) and brine (100 mL). Dry (MgSO$_4$) and evaporate the solvent in vacuo to give the title compound.

Step d: DL-4,6-Dibromotryptophan

Mix DL-4,6-dibromotryptophan ethyl ester (1.20 g, 3.07 mmol), triethylamine (341 mg, 3.38 mmol) and methylene chloride (50 mL). Add benzyl chloroformate (692 mg, 4.06 mmol) and stir for 12 hours. Dilute with methylene chloride, wash with 1M hydrochloric acid (100 mL) and brine (100 mL). Dry (MgSO$_4$) and evaporate the solvent in vacuo and purify by silica gel chromatography to give DL-4,6-dibromotryptophan-benzyloxycarbonyl ethyl ester.

Mix DL-4,6-dibromotryptophan-benzyloxycarbonyl ethyl ester (440 mg, 0.84 mmol) in 1:1 tetrahydrofuran/water (50 mL) and add lithium hydroxide monohydrate (106 mg, 2.52 mmol). Stir at room temperature for 2 hours. Pour into 1M hydrochloric acid (150 mL) and extract with ethyl acetate (200 mL). Dry (MgSO$_4$) and evaporate the solvent in vacuo to give DL-4,6-dibromotryptophan-benzyloxycarbonyl.

Dissolve DL-4,6-dibromotryptophan-benzyloxycarbonyl (407 mg, 0.82 mmol) in chloroform (50 mL) and add trimethylsilyl iodide (656 mg, 3.28 mmol). Stir at room temperature for 1.5 hours and pour the resulting violet solution into isopropanol (50 mL) containing a small amount of DL-dithiothreitol. Neutralize with propylene oxide to give a white semi-solid. Take this mixture up in 1M hydrochloric acid (200 mL), treat with charcoal and wash with methylene chloride. Evaporate the water in vacuo. Dissolve the solid in methanol (50 mL) and neutralize with propylene oxide. Add ethyl ether and filter to give the title compound.

The following compounds can be prepared analogously to that described in Example 1–2:

DL-4-Bromo-6-fluorotryptophan;
DL-4-Bromo-6-chlorotryptophan;
DL-4-Ethyl-6-bromotryptophan.

The compounds of Formula Ib may be prepared using techniques and procedures well known and appreciated by one of ordinary skill in the art. A general synthetic procedure for preparing these compounds is set forth in Scheme B. In Scheme B, all substituents unless otherwise indicated are as previously defined.

Scheme B provides a general synthetic scheme for preparing compounds of Formula Ib.

In step a, the appropriate 3,5-disubstituted aniline of structure (7) is iodinated to give the corresponding 2-iodo-3,5-disubstituted-aniline of structure (8).

For example, the appropriate 3,5-disubstituted aniline of structure (7) is contacted with a molar equivalent of an appropriate iodinating agent such as N-iodosuccinimide. The reactants are typically contacted in a suitable acidic organic solvent such as acetic acid/methylene chloride. The reactants are typically stirred together at room temperature in the absence of light for a period of time ranging from 5–24 hours. The 2-iodo-3,5-disubstituted-aniline of structure (8) is recovered from the reaction zone by extractive methods as is known in the art. It may be purified by silica gel chromatography.

Alternatively, an appropriate 2-iodo-3,5-disubstituted-aniline of structure (8) may be prepared from an appropriate 2,4-disubstituted-b-nitroaniline.

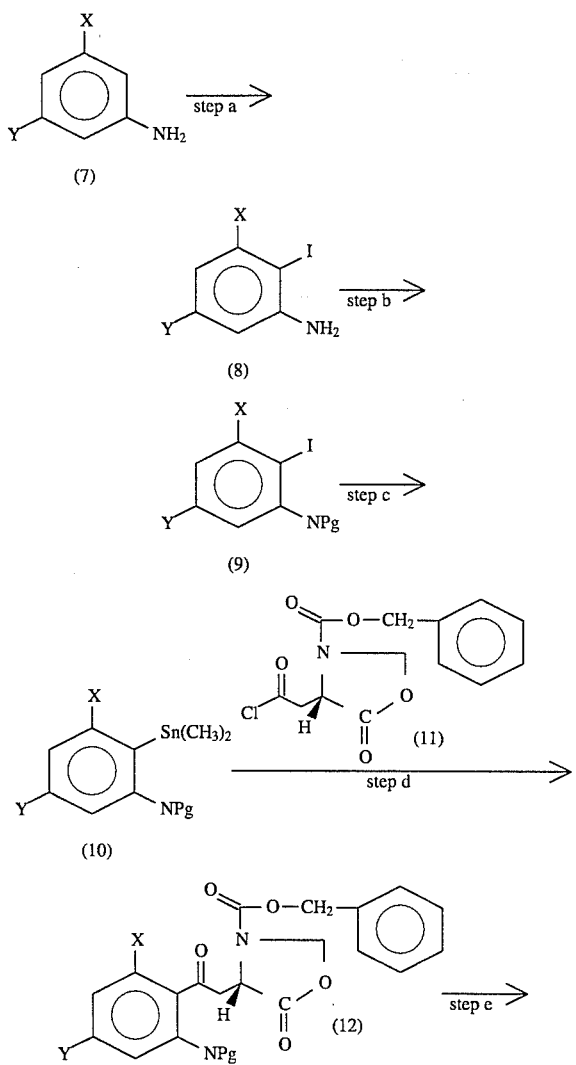

Scheme B

-continued
Scheme B

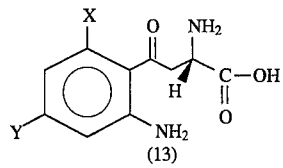

First, an appropriate 2,4-disubstituted-6-nitroaniline is iodinated as is known in the art, such as 50% sulfuric acid, sodium nitrite and potassium iodide, to give the corresponding 2-iodo-3,5-disubstituted-nitrobenzene.

Second, the nitro functionality of an appropriate 2-iodo-3,5-disubstituted-nitrobenzene is reduced as is known in the art, such as tin (II) chloride dihydrate, to give the corresponding 2-iodo-3,5-disubstituted-aniline of structure (8).

In step b, appropriate 2-iodo-3,5-disubstituted-aniline of structure (8) is protected to give the N-protected-3,5-disubstituted-2-iodoaniline of structure (9). The selection and utilization of appropriate protecting groups are well known to one of ordinary skill in the art and are described in "Protective Groups in Organic Synthesis", Theodora W. Greene, Wiley (1981).

In step c, the appropriate N-protected-3,5-disubstituted-2-iodoaniline of structure (9) is converted to the corresponding N-protected-3,5-disubstituted-2-(trimethylstannyl)aniline of structure (10).

For example, the appropriate N-protected-3,5-disubstituted-2-iodoaniline of structure (9) is contacted with a molar excess of an appropriate stannylating agent, such as hexamethylditin, a molar excess of a non-nucleophilic base, such as N-methylmorpholine or sodium hydride, and a catalytic amount of a palladium(0) reagent such as tris(dibenzylideneacetone)dipalladium(0) or $Pd(CN)_2Cl_2$. The reactants are typically contaced in a suitable organic solvent such as toluene. The reactants are typically stirred together for a period of time ranging from 10–45 hours and at a temperature range of from 40°–80° C. The N-protected-3,5-disubstituted-2-(trimethylstannyl)aniline of structure (10) is recovered from the reaction zone and purified by silica gel chromatography.

In step d, the appropriate N-protected-3,5-disubstituted-2-(trimethylstannyl)aniline of structure (10) is reacted with (S)-3-(benzyloxycarbonyl)-5-oxo-4-oxazolidineacetyl chloride (11) to give the corresponding N-protected-2-[1-oxo-2-[(S)-3-(benzyloxycarbonyl)-5-oxo-4-oxazoldine-2-yl]ethyl]-3,5-disubstituted-aniline of structure (12).

For example, the appropriate N-protected-3,5-disubstituted-2-(trimethylstannyl)aniline of structure (10) is contacted with a molar equivalent of (S)-3-(benzyloxycarbonyl)-5-oxo-4-oxazolidineacetyl chloride (11). The reactants are typically contacted in a suitable organic solvent such as toluene. The reactants are typically stirred together for a period of time ranging from 1–5 hours and at a temperature range of from room temperature to 60° C. The N-protected-2-[1-oxo-2-[(S)-3-(benzyloxycarbonyl)-5-oxo-4-oxazoldine-2-yl]ethyl]-3,5-disubstituted-aniline of structure (12) is recovered from the reaction zone and purified by silica gel chromatography.

In step e, the appropriate N-protected-2-[1-oxo-2-[(S)3-(benzyloxycarbonyl)-5-oxo-4-oxazoldine-2-yl]ethyl]-3,5-disubstituted-aniline of structure (12) is deprotected to give the 4,6-disubstituted-kynurenine of structure (13).

For example, the appropriate N-protected-2-[1-oxo-2[(S)-3-(benzyloxycarbonyl)-5-oxo-4-oxazoldine-2-yl]ethyl]3,5-disubstituted-aniline of structure (12) is contacted with a molar excess of trimethylsilyl iodide. The reactants are typically contacted in a suitable organic solvent such as chloroform. The reactants are typically stirred together at room temperature for a period of time ranging from 1–5 hours. The 4,6-disubstituted-kynurenine of structure (13) is recovered from the reaction zone by extractive methods as is known in the art.

Alternatively, the compounds may be sequentially deprotected with TFA to remove the Boc group, in NaOH to diesterity and TMSI to remove the CBZ group.

Starting materials for use in Scheme B are readily available to one of ordinary skill in the art. For example, (S)-3-(benzyloxycarbonyl)-5-oxo-4-oxazolidineacetyl chloride (11) is described in *J. Org. Chem.* 53 6138–39 1988.

The following examples present typical syntheses as described in Scheme B. These examples are understood to be illustrative only and are not intended to limit the scope of the present invention in any way.

EXAMPLE 3

L-4,6-Dichlorokynurenine

Step a: 2-Iodo-3,5-dichloroaniline

Dissolve 3,5-dichloroaniline (10 g, 61.5 mmol) in 1:1 acetic acid/methylene chloride (200 mL). Add N-iodosuccinimide (16.9 g, 61.5 mmol) as a solid and stir at room temperature in the absence of light for 8 hours. Pour the solution into saturated sodium hydrogen carbonate (200 mL) and extract into methylene chloride (100 mL). Wash with saturated sodium hydrogen carbonate (200 mL), dry ($MgSO_4$) and evaporate the solvent in vacuo. Purify by silica gel chromatography to give the title compound (8.1 g, 45%); mp 61°–63° C.

$^1$H NMR ($CDCl_3$) 4.4 ppm (2H, bs), 6.70 ppm (1H, d), 6.88 ppm (1H, d); $^{13}$C NMR ($CDCl_3$) ppm: 85.77, 111.75, 118.47, 135.21, 139.78, 149.48.

Anal. Calcd for $C_6H_4Cl_2IN$: C, 25.03; H, 1.40; N, 4.87; Found: C, 25.33; H, 1.36; N, 4.87.

Step b: N-(t-butoxycarbonyl)-3,5-dichloro-2-iodoaniline

Mix 2-iodo-3,5-dichloroaniline (11.67 g, 40.5 mmol), di-tert-butyldicarbonate (44 g, 203 mmol) and a catalytic amount of dimethylaminopyridine. Stir for 4 hours at room temperature, take up in ethyl acetate (200 mL), wash with 1M hydrochloric acid (200 mL), saturated sodium chloride (100 mL) and dry ($MgSO_4$). Evaporate the solvent in vacuo and purify by silica gel chromatography to give N-(bis-t-butoxycarbonyl)- 3,5-dichloro-2-iodoaniline as a white solid (17.4 g, 87%); mp 131°–132° C.

$^1$H NMR ($CDCl_3$/TMS) 1.45 ppm (18H, s), 7.11 ppm (1H, d), 7.41 ppm (1H, d); $^{13}$C NMR ($CDCl_3$) ppm: 27.87, 83.22, 103.18, 127.31, 128.07, 134.66, 140.08, 144.80, 149.63.

Anal. Calcd for $C_{16}H_{20}Cl_2INO_4$: C, 39.37, H, 4.13; N, 2.87; Found: C, 39.37; H, 4.20; N, 3.12.

Mix N-(bis-t-butoxycarbonyl)-3,5-dichloro-2-iodoaniline (17.39 g, 35.64 mmol), potassium carbonate (6.4 g, 46 mmol) and ethanol (200 mL). Heat for 5 hours, pour into water (200 mL), extract into ethyl acetate (150 mL) and dry ($MgSO_4$). Evaporate the solvent in vacuo and purify by silica gel chromatography (10:1 hexane/ethyl acetate) to give the title compound as a white crystaline solid (12.56 g, 91%); mp 64°–66° C. $^1$H NMR ($CDCl_3$/TMS) 1.60 ppm (9H, s), 7.1 ppm (1H, bs), 7.19 ppm (1H, d), 8.12 ppm (1H, d).

Step c: N-(t-butoxycarbonyl)-3,5-dichloro-2-(trimethylstannyl)aniline

Mix sodium hydride (413 mg of a 60% suspension in mineral oil, 10.32 mmol) and 1-methyl-2-pyrrolidinone (5 mL). Place under an argon atmosphere and cool to 0° C. Add a solution of N-(t-butoxycarbonyl)-3,5-dichloro-2-iodoaniline (3.33 g, 8.60 mmol) in 1-methyl-2-pyrrolidinone (50 mL). Stir at 0° C. for 15 minutes, then for 30 minutes at room temperature. Cool to 0° C. and add hexamethylditin (6.7 g, 21 mmol) followed by Pd(CN)$_2$Cl$_2$ (223 mg). Stir for 5 minutes, dilute the resulting black solution with diethyl ether (100 mL) and pass through a bed of Celite filter aid. Wash the solution with saturated sodium chloride (2×100 mL), water (100 mL) and dry (MgSO$_4$). Evaporate the solvent in vacuo and purify by silica gel chromatography (14:1 hexane/ethyl acetate) to give the title compound as a white crystalline solid (2.20 g, 60%).

$^1$H NMR (CDCl$_3$/TMS) 0.50 ppm (9H, s), 1.51 ppm (9H, s), 6.75 ppm (1H, bs), 7.05 ppm (1H, d), 7.70 ppm (1H, d).

Step d: N-(t-butoxycarbonyl)-2-[1-oxo-2-[(S)-3-(benzyloxycarbonyl)-5-oxo-4-oxazoldine-2-yl]ethyl]-3,5-dichloroaniline Mix (S)-3-(benzyloxycarbonyl)-5-oxo-4-oxazolidineacetyl chloride (1.85 g, 6.21 mmol), powdered 4A molecular sieves (4 g) and toluene (50 mL). Stir under an argon atmosphere for 1 hour. Add a solution of N-(t-butoxycarbonyl)-3,5-dichloro-2-(trimethylstannyl)aniline (2.20 g, 5.18 mmol) in toluene (50 mL) followed by Pd(CN)$_2$Cl$_2$ (134 mg). Heat to 80° C. for 1.5 hours, cool and purify directly by silica gel chromatography (3:1 hexane/ethyl acetate) to give the title compound as a colorless oil (1.42 g, 53%).

$^1$H NMR (CDCl$_3$/TMS) 1.50 ppm (9H, s), 3.50 ppm (1H, dd), 3.8–4.1 ppm (1H, m), 4.5 ppm (1H, bs), 5.25 ppm (2H, dd), 5.35 ppm (1H, dd), 5.5–5.7 ppm (1H, bs), 7.05 ppm (1H, bs), 7.45 ppm (5H, s), 7.85 ppm (1H, d), 8.15 ppm (1H, d).

Step e: L-4,6-Dichlorokynurenine

Dissolve N-(t-butoxycarbonyl)-2-[1-oxo-2-[(S)-3-(benzyloxycarbonyl)-5-oxo-4-oxazoldine-2-yl]ethyl]-3,5-dichloroaniline (700 mg, 1.34 mmol) in methylene chloride (50 mL) and treat with trifluoroacetic acid (20 mL). Stir for 3 hours, pour into saturated sodium hydrogen carbonate (100 mL) and extract into methylene chloride (100 mL). Wash with saturated sodium hydrogen carbonate (100 mL), saturated sodium chloride (100 mL) and dry (MgSO$_4$). Evaporate the solvent in vacuo and purify by silica gel chromatography (3:1 hexane/ethyl acetate) to give 2-[1-oxo-2-[(S)-3-(benzyloxycarbonyl)-5-oxo-4-oxazoldine-2-yl]ethyl]-3,5-dichloroaniline as a pale yellow oil (380 mg, 67%).

$^1$H NMR (CDCl$_3$/TMS) 3.60 ppm (1H, dd), 4.0–4.3 ppm (1H, m), 4.45 ppm (1H, bs), 4.9–5.3 ppm (2H, bs), 5.25 ppm (2H, dd), 5.45 ppm (1H, dd), 5.6 ppm (1H, bs), 6.55 ppm (1H, d), 6.70 ppm (1H, d), 7.45 ppm (5H, s).

Dissolve 2-[1-oxo-2-[(S)-3-(benzyloxycarbonyl)-5-oxo-4-oxazoldine-2-yl]ethyl]-3,5-dichloroaniline (380 mg, 0.90 mmol) in methanol (10 mL) and treat with 1N sodium hydroxide (0.99 mL, 0.99 mmol). Stir for 6 hours, pour into 1M hydrochloric acid (100 mL) and extract with ethyl acetate (100 mL). Dry (MgSO$_4$) and evaporate the solvent in vacuo. Purify by silica gel chromatography (1 to 5% methanol in chloroform) to give N-(benzyloxycarbonyl)-L-4,6-dichlorokynurenine as a yellow oil (157 mg, 43%).

$^1$H NMR (CDCl$_3$/TMS) 3.65 ppm (2H, dd), 4.80 ppm (1H, m), 5.15 ppm (2H, dd), 5.9 ppm (1H, d), 6.0–6.2 ppm (2H, bs), 6.50 ppm (1H, d), 6.70 ppm (1H, d), 7.35 ppm (5H, s).

Dissolve N-(benzyloxycarbonyl)-L-4,6-dichlorokynurenine (157 mg, 0.43 mmol) in chloroform (30 mL) and add trimethylsilyl iodide (426 mg, 2.13 mmol). Stir under an argon atmosphere for 1 hour, quench with methanol and evaporate the solvent in vacuo. Take up the resulting red oil in isopropanol (10 mL) containing a trace amount of DL-dithiothreitol. Treat the resulting pale yellow solution with propylene oxide (122 mg, 2.13 mmol) to give the title compound as a yellow solid. Wash with diethyl ether (500 mL) and dry at 60° C. under 1 mm Hg to give the title compound (67 mg, 57%).

$^1$H NMR (DMSO-d6/TMS) 2.90 ppm (1H, dd), 3.20 ppm (1H, dd), 4.85 ppm (1H, dd), 6.6 ppm (1H, d), 6.65 ppm (1H, d), 6.7 ppm (2H, s), 7.5–8.0 ppm (3H, bs); MS (FAB) m/e 277 (M+H, 100), 260 (5), 188 (15).

EXAMPLE 4

4-fluoro-6-Bromo-kynurenine

Step a: 2-Iodo-3-bromo-5-fluoroaniline

Mix 4-fluoro-2-nitroaniline (15.6 g, 0.1 mol) in water (400 mL) and add 48% hydrobromic acid (1 kg). Add bromine (16 g, 0.1 mol) with stirring and stir for 1 hour. Dilute to 2 L and cool to 7° C. Filter, wash with water and dry to give fluoro-2-bromo-6-nitroaniline.

Mix 4-fluoro-2-bromo-6-nitroaniline (15.5 g, 66.0 mmol) and 50% sulfuric acid (200 mL) and cool to 0°–5° C. Add, by dropwise addition, a solution of sodium nitrite (6.0 g, 86.4 mmol) in water (50 mL). Stir for 30 minutes and add solid potassium iodide (29 g, 173 mmol). Take up the product in ethyl acetate (300 mL) wash with saturated sodium hydrogen carbonate (2×200 mL), saturated sodium metabisulfite (2×200 mL) and water (200 mL). Dry (MgSO$_4$), evaporate the solvent in vacuo and purify by silica gel chromatography to give 1-iodo-2-nitro-4-fluoro-6-bromobenzene as a yellow crystalline solid (17.81 g, 76%); mp 75°–76° C.

$^1$H NMR (CDCl$_3$/TMS) 7.35 ppm (1H, dd), 7.65 ppm (1H, dd); $^{13}$C NMR (CDCl$_3$) ppm: 111.23, 111.58, 122.98, 123.31, 133.82, 133.94.

Anal. Calcd for C$_6$H$_2$BrFINO$_2$: C, 20.83; H, 0.58; N, 4.05; Found: C, 21.02; H, 0.74; N, 4.24.

Treat 1-iodo-2-nitro-4-fluoro-6-bromobenzene (5.0 g, 14.46 mmol) with tin (II) chloride dihydrate (12 g, 58 mmol) in refluxing ethanol (150 mL). Stir at reflux for 24 hours, pour into a mixture of ethyl acetate (200 mL) and saturated sodium hydrogen carbonate (500 mL). Filter and wash the filtrate with saturated sodium hydrogen carbonate (200 mL) and water (200 mL). Dry (MgSO$_4$), evaporate the solvent in vacuo and purify by silica gel chromatography to give the title compound as an off-white solid (3.45 g, 76%).

$^1$H NMR (CDCl$_3$/TMS) 4.5 ppm (2H, bs), 6.45 ppm (1H, dd), 7.85 ppm (1H, dd).

Step b: N-(t-butoxycarbonyl)-3-bromo-5-fluoro-2-iodoaniline

Mix 2-Iodo-3-bromo-5-fluoroaniline (3.00 g, 9.5 mmol), di-tert-butyldicarbonate (4.15 g, 19 mmol) and a catalytic amount of dimethylaminopyridine. Stir for 4 hours at room temperature, take up in ethyl acetate, wash with 1M hydrochloric acid, saturated sodium chloride and dry (MgSO$_4$). Evaporate the solvent in vacuo and purify by silica gel chromatography to give N-(bis-t-butoxycarbonyl)-3-bromo-5-fluoro-2-iodoaniline as a white solid (4.36 g, 90%).

¹H NMR (CDCl₃/TMS) 1.45 ppm (18H, s), 6.95 ppm (1H, dd), 7.40 ppm (1H, dd).

Mix N-(bis-t-butoxycarbonyl)-3-bromo-5-fluoro-2-iodoaniline (4.00 g, 7.75 mmol), potassium carbonate (10 mmol) and ethanol (50 mL). Heat for 5 hours, pour into water (50 mL), extract into ethyl acetate (40 mL) and dry (MgSO₄). Evaporate the solvent in vacuo and purify by silica gel chromatography to give the title compound as a white crystaline solid (2.66 g, 83%).

¹H NMR (CDCl₃/TMS) 1.55 ppm (9H, s), 7.15 ppm (1H, dd), 7.20 ppm (1H, bs), 7.95 ppm (1H, dd).

Step c: N-(t-butoxycarbonyl)-3-bromo-5-fluoro-2-(trimethylstannyl)aniline

Mix sodium hydride (317 mg of a 60% suspension in mineral oil, 7.9 mmol) and 1-methyl-2-pyrrolidinone (5 mL). Place under an argon atmosphere and cool to 0° C. Add a solution of N-(t-butoxycarbonyl)-3-bromo-5-fluoro-2-iodoaniline (2.50 g, 6.10 mmol) in 1-methyl-2-pyrrolidinone (50 mL). Stir at 0° C. for 15 minutes, then for 30 minutes at room temperature. Cool to 0° C. and add hexamethylditin (9.8 g, 30 mmol) followed by Pd(CN)₂Cl₂ (223 mg). Stir for 5 minutes, dilute the resulting black solution with diethyl ether (100 mL) and pass through a bed of Celite filter aid. Wash the solution with saturated sodium chloride (2×100 mL), water (100 mL) and dry (MgSO₄). Evaporate the solvent in vacuo and purify by silica gel chromatography to give the title compound as a white solid (1.50 g, 54%).

¹H NMR (CDCl₃/TMS) 0.50 ppm (9H, s), 1.50 ppm (9H, s), 6.80 ppm (1H, bs), 7.00 ppm (1H, dd), 7.65 ppm (1H, dd).

Step d: N-(t-butoxycarbonyl)-2-[1-oxo-2-[(S)-3-(benzyloxycarbonyl)-5-oxo-4-oxazoldine-2-yl]ethyl],3-bromo-5-fluoroaniline Mix (S)-3-(benzyloxycarbonyl)-5-oxo-4-oxazolidineacetyl chloride (946 g, 3.18 mmol), powdered 4A molecular sieves (4 g) and toluene (50 mL). Stir under an argon atmosphere for 1 hour. Add a solution of N-(t-butoxycarbonyl)-3-bromo-5-fluoro-2-(trimethylstannyl)aniline (1.44 g, 3.18 mmol) in toluene (50 mL) followed by Pd(CN)₂Cl₂ (134 mg). Heat to 80° C. for 1.5 hours, cool and purify directed by silica gel chromatography (3:1 hexane/ ethyl acetate) to give the title compound as a white crystalline solid (123 mg, 7%).

¹H NMR (CDCl₃/TMS) 1.55 ppm (9H, s), 3.45–4.25 ppm (2H, m), 4.45 ppm (1H, bs), 5.20 ppm (2H, m), 5.4–5.6 ppm (2H, m), 7.00 ppm (1H, m), 7.35–7.45 ppm (6H, bs), 7.90 ppm (1H, m).

Step e: L-6-Bromo-4-fluorokynurenine

Dissolve N-(t-butoxycarbonyl)-2-[1-oxo-2-[(S)-3-(benzyloxycarbonyl)-5-oxo-4-oxazoldine-2-yl]ethyl]-3-bromo-5-fluoroaniline (1.34 mmol) in methylene chloride (50 mL) and treat with trifluoroacetic acid (20 mL). Stir for 3 hours, pour into saturated sodium hydrogen carbonate (100 mL) and extract into methylene chloride (100 mL). Wash with saturated sodium hydrogen carbonate (100 mL), saturated sodium chloride (100 mL) and dry (MgSO₄). Evaporate the solvent in vacuo and purify by silica gel chromatography (3:1 hexane/ethyl acetate) to give 2-[1-oxo-2-[(S)-3-(benzyloxycarbonyl)-5-oxo-4-oxazoldine-2-yl]ethyl]-3-bromo-5-fluoroaniline.

Dissolve 2-[1-oxo-2-[(S)-3-(benzyloxycarbonyl)-5-oxo-4-oxazoldine-2-yl]ethyl]-3-bromo-5-fluoroaniline (0.90 mmol) in methanol (10 mL) and treat with 1N sodium hydroxide (0.99 mL, 0.99 mmol). Stir for 6 hours, pour into 1M hydrochloric acid (100 mL) and extract with ethyl acetate (100 mL). Dry (MgSO₄) and evaporate the solvent in vacuo. Purify by silica gel chromatography (1 to 5% methanol in chloroform) to give N-(benzyloxycarbonyl)-L-6-bromo-4-fluorokynurenine.

Dissolve N-(benzyloxycarbonyl)-L-6-bromo-4-fluorokynurenine (0.43 mmol) in chloroform (30 mL) and add trimethylsilyl iodide (426 mg, 2.13 mmol). Stir under an argon atmosphere for 1 hour, quench with methanol and evaporate the solvent in vacuo. Take up the resulting residue in isopropanol (10 mL) containing a trace amount of DL-dithiothreitol. Treat the solution with propylene oxide (122 mg, 2.13 mmol) to give the title compound.

The following compounds can be prepared analogously to those described in Examples 3 and 4:

6-Bromo-4-chlorokynurenine;

6-Bromo-4-bromokynurenine;

6-Ethyl-4-bromokynurenine.

An alternate synthetic procedure for preparing compounds of Formula Ib is outlined in Scheme C. In Scheme C, all substituents unless otherwise indicated, are as previously defined.

Scheme C provides an alternate synthetic procedure for preparing compounds of Formula Ib.

In step a, the appropriate 4,6-substituted tryptophan ethyl ester of structure (5) is protected to give the 4,6-substituted-tryptophan-benzyloxycarbonyl ethyl ester of structure (14) as described previously in Scheme A, step d.

In step b, the appropriate 4,6-substituted tryptophan-benzylcarbonyl ethyl ester of structure (14) is oxidatively cleaved to give the N-(benzyloxycarbonyl)-3,5-disubstituted-kynurenine ethyl ester of structure (15).

For example, the appropriate 4,6-substituted tryptophan-benzyloxycarbonyl ethyl ester of structure (14) is contacted with a molar excess of an oxidating agent such as 4-t-butyl iodylbenzene. The reactants are typically contacted in a suitable organic solvent such as chlorobenzene. The reactants are typically stirred together for a period of time ranging from 2–24 hours and at a temperature range of from room temperature to reflux. The N-(benzyloxycarbonyl)-3,5-disubstituted-kynurenine ethyl ester of structure (15) is recovered from the reaction zone by evaporate of the solvent. It can be purified by silica gel chromatography.

Scheme C

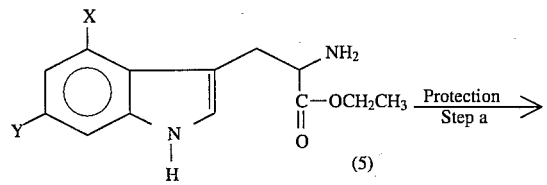

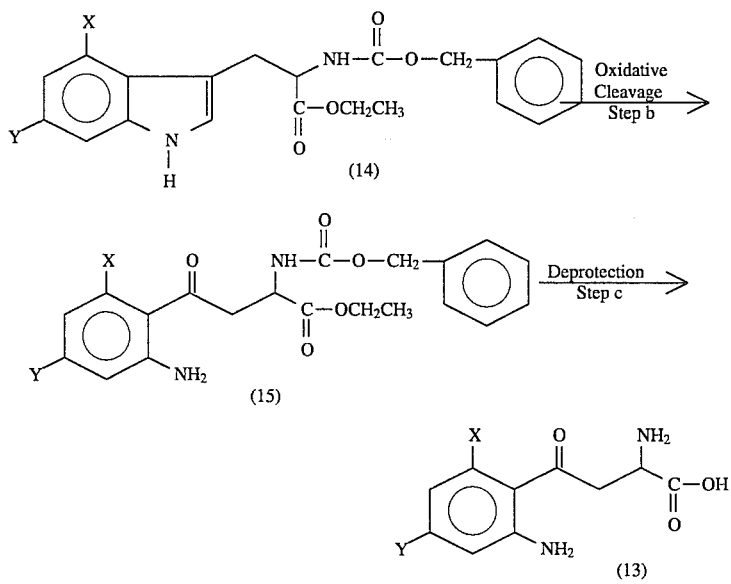

Alternatively, the appropriate 4,6-disubstituted tryptophan-benzylcarbonyl ethyl ester of structure (14) may be oxidatively cleaved with ozone as is known in the art to give an intermediate N-(benzyloxycarbonyl)-3,5-disubstituted-N-formyl-kynurenine. The N-formyl functionality of the intermediate N-(benzyloxycarbonyl)-3,5-disubstituted-N-formyl-kynurenine is then removed by acid hydrolysis to give the corresponding N-(benzyloxycarbonyl)- 3,5-disubstituted-kynurenine ethyl ester of structure (15).

In step c, the protecting groups of the appropriate N-(benzyloxycarbonyl)-3,5-disubstituted-kynurenine ethyl ester of structure (15) are removed to give the corresponding 3,5-disubstituted-kynurenine of structure (13) as described previously in Scheme A, step d.

Starting materials for use in Scheme C are readily available to one of ordinary skill in the art. For example, 4-t-butyl iodylbenzene is described in *J. Chem. Soc., Chem. Commun.* 1887–88.

The following examples present typical syntheses as described in Scheme C. These examples are understood to be illustrative only and are not intended to limit the scope of the present invention in any way.

EXAMPLE 5

4,6-Dibromokynurenine

Step a: N-(Benzyloxycarbonyl)-4,6-dibromotryptophan ethyl ester

Mix DL-4,6-dibromotryptophan ethyl ester (1.20 g, 3.07 mmol), triethylamine (341 mg, 3.38 mmol) and methylene chloride (50 mL). Add benzyl chloroformate (692 mg, 4.06 mmol) and stir for 12 hours. Dilute with methylene chloride, wash with 1M hydrochloric acid (100 mL) and brine (100 mL). Dry (MgSO$_4$) and evaporate the solvent in vacuo and purify by silica gel chromatography to give the title compound.

Step b: N-(Benzyloxycarbonyl)-4,6-dibromokynurenine ethyl ester

Dissolve N-(benzyloxycarbonyl)-4,6-dibromotryptophan ethyl ester (1.05 g, 2 mmol) in chlorobenzene (8 mL) and mix with 4-t-butyl iodylbenzene (876 g, 3 mmol). Reflux for 4 hours and evaporate the solvent in vacuo. Purify by silica gel chromatography to give the title compound.

Step c: 4,6-Dibromokynurenine

Mix N-(benzyloxycarbonyl)-4,6-dibromokynurenine ethyl ester (444 mg, 0.84 mmol) in 1:1 tetrahydrofuran/water (50 mL) and add lithium hydroxide monohydrate (106 mg, 2.52 mmol). Stir at room temperature for 2 hours. Pour into 1M hydrochloric acid (150 mL) and extract with ethyl acetate (200 mL). Dry (MgSO$_4$) and evaporate the solvent in vacuo to give N-(benzyloxycarbonyl)-4,6-dibromokynurenine.

Dissolve N-(benzyloxycarbonyl)-4,6-dibromokynurenine (410 mg, 0.82 mmol) in chloroform (50 mL) and add trimethylsilyl iodide (656 mg, 3.28 mmol). Stir at room temperature for 1.5 hours and pour the resulting violet solution into isopropanol (50 mL) containing a small amount of DL-dithiothreitol. Neutralize with propylene oxide to give a white semi-solid. Take this mixture up in 1M hydrochloric acid (200 mL), treat with charcoal and wash with methylene chloride. Evaporate the water in vacuo to give a white solid. Dissolve the white solid in methanol (50 mL) and neutralize with propylene oxide. Add ethyl ether and filter to give the title compound.

EXAMPLE 6

4,6-Dichlorokynurenine (See Example 3)

Step b: N-(Benzyloxycarbonyl)-4,6-dichlorokynurenine ethyl ester ester

Dissolve DL-4,6-dichlorotryptophan-benzyloxycarbonyl ethyl ester (1.90 g, 4.42 mmol) in methanol (200 mL), cool to –78° C. and treat with ozone until a blue color is observed (approximately 3–5 minutes). Purge with nitrogen gas and quench with dimethylsulfide (10 mL). Evaporate the solvent in vacuo, take up in diethyl ether and wash with water (2×150 mL) and brine (200 mL). Dry (MgSO$_4$) and evaporate the solvent in vacuo to give N-(formyl)-2-[ethyl-4-oxo-2-(benzyloxycarbonylamino)butyrate-4-yl]-3,5-dichloroaniline as an amber oil (1.98 g, 96%).

$^1$H NMR (CDCl$_3$/TMS) 1.25 ppm (3H, t), 3.55 ppm (2H, d), 4.25 (2H, q), 5.80 ppm (1H, m), 5.15 ppm (2H, s), 5.80 ppm (1H, bs), 7.19 ppm (1H, d), 7.35 ppm (5H, s), 8.30 ppm (1H, d), 8.40 ppm (1H, s), 8.75 ppm (1H, bs).

Dissolve N-(formyl)-2-[ethyl-4-oxo-2-(benzyloxycarbonylamino)butyrate-4-yl]-3,5-dichloroaniline (1.94 g, 4.15 mmol) in methanol (200 mL) and treat with 4N hydrochloric acid/dioxane (8.3 mmol). Stir for 1 hour, pour into saturated sodium hydrogen carbonate (200 mL) and extract into ethyl acetate (150 mL). Dry (MgSO$_4$) and evaporate the solvent in vacuo to give the title compound as a yellow oil (1.82 g, 100%)

$^1$H NMR (CDCl$_3$/TMS) 1.35 ppm (3H, t), 3.65 ppm (2H, dd), 4.25 ppm (2H, q), 4.70 ppm (1H, m), 5.15 ppm (4H, bs), 5.80 ppm (1H, d), 6.55 ppm (1H, d), 6.70 ppm (1H, d), 7.35 ppm (5H, s).

Step c: 4,6-Dichlorokynurenine

Dissolve N-(benzyloxycarbonyl)-4,6-dichlorokynurenine ethyl ester (1.82 g, 4.14 mmol) in a 1:1 mixture of tetrahydrofuran/water (100 mL). Treat with lithium hydroxide monohydrate (522 mg, 12.4 mmol) and warm at 70° C. for 4 hours. Pour into 1M hydrochloric acid (100 mL) and extract into ethyl acetate (150 mL). Dry (MgSO$_4$) and evaporate the solvent in vacuo to give N-(benzyloxycarbonyl)-4,6dichlorokynurenine as a yellow foam (1.52 g, 89%).

$^1$H NMR (CDCl$_3$/TMS) 3.50–3.80 ppm (2H, dd), 4.80 ppm (1H, m), 5.15 ppm (2H, bs), 6.0 ppm (1H, d), 6.55 ppm (1H, d), 6.70 ppm (1H, d), 7.00 ppm (3H, bs), 7.35 ppm (5H, s).

Dissolve N-(benzyloxycarbonyl)-4,6-dichlorokynurenine (1.52 g, 3.70 mmol) in chloroform (100 mL) and add trimethylsilyl iodide (3.7 g, 18.5 mmol). Stir at room temperature under an argon atmosphere for 1 hour, quench with methanol and evaporate the solvent in vacuo. Take up the resulting red oil into isopropanol (10 mL) containing a small amount of DL-dithiothreitol. Neutralize the resulting pale yellow solution with propylene oxide (1.0 g, 18.5 mmol) to give a yellow solid. Wash with diethyl ether (500 mL) and dry at 60° C. under 1 mm Hg to give the title compound (870 mg, 85%).

$^1$H NMR (DMSO-d6/TMS) 2.90 ppm (1H, dd), 3.15–3.25 ppm (1H, m), 3.85 ppm (1H, dd), 6.60 ppm (1H, d), 6.70 ppm (1H, d), 6.75 ppm (2H, s), 7.6–7.9 ppm (3H, bs); MS (FAB) m/e 277 (M+H, 100), 260 (15), 188 (55); HRMS (FAB) Calcd. for C$_{10}$H$_{11}$Cl$_2$N$_2$O$_3$: M+H 277.01467. Found: M+H 277.0160.

The compounds of Formula IIa and IIb are known in the art. Methods for preparing these compounds are known in the art.

As noted above, the compounds of Formula Ia, Ib, IIa, and IIb (hereinafter "the compounds") antagonize the effects which excitatory amino acids have upon the NMDA receptor complex. This antagonist effect can be demonstrated by their ability to prevent NMDA-stimulated cyclic GMP accumulation in neonatal rat cerebellar tissue. This test is based upon the phenomenon that when samples of neonatal rat cerebellar tissue are exposed to the agonist, NMDA, there is an increase in cyclic GMP levels within this tissue. NMDA antagonists inhibit or decrease this rise in cyclic GMP levels. This test can be performed by methods similar to those of Baron et al., J. Pharmacol. Exp. Ther. Vol 250 page 162 (1989).

The compounds exhibit anti-convulsant properties and are useful in the treatment of epilepsy. They are useful in the treatment of grand mal seizures, petit mal seizures, psychomotor seizures, autonomic seizures, etc. One method of demonstrating their anti-epileptic properties is by their ability to inhibit the seizures that are caused by the administration of quinolinic acid, an NMDA agonist. This test can be conducted in the following manner.

One group containing ten mice are administered 0.01–100 μg of test compound intracerebroventricularly in a volume of 5 microliters of saline. A second control group containing an equal number of mice are administered an equal volume of saline as a control. Approximately 5 minutes later, both groups are administered 7.7 micrograms of quinolinic acid intracerebroventricularly in a volume of 5 microliters of saline. The animals are observed for 15 minutes thereafter for signs of clonic-tonic seizures. The control group will have a statistically higher rate of clonic-tonic seizures than will the test group.

The compounds are useful for preventing or minimizing the damage which nervous tissues contained within the CNS suffer upon exposure to either ischemic, hypoxic, or hypoglycemic conditions or as the result of physical trauma. Representative examples of such conditions include strokes or cerebrovascular accidents, hyperinsulinemia, cardiac arrest, physical trauma, drownings, suffocation, and neonatal anoxic trauma. The compounds should be administered to the patient within 24 hours of the onset of the hypoxic, ischemic, or hypoglycemic condition in order for the compounds to effectively minimize the CNS damage which the patient will experience.

The compounds are also useful in the treatment of neurodegenerative diseases such as Huntington's disease, Alzheimer's disease, senile dementia, glutaric acidaemia type I, Parkinson's disease, multi-infarct dementia, and neuronal damage associated with uncontrolled seizures. The administration of these compounds to a patient experiencing such a condition will serve to either prevent the patient from experiencing further neurodegeneration or it will decrease the rate at which the neurodegeneration occurs.

As is apparent to those skilled in the art, the compounds will not correct any CNS damage that has already occurred as the result of either disease, or a lack of oxygen or sugar. As used in this application, the term "treat" refers to the ability of the compounds to prevent further damage or delay the rate at which any further damage occurs.

The compounds exhibit an anxiolytic effect and are thus useful in the treatment of anxiety. The compounds also exhibit an analgesic effect and are useful in controlling pain. The compounds may be co-administered with a narcotic analgesic such as morphine, demerol, etc. In addition to lowering the dose of narcotic required, the compounds decrease the rate at which patients develop tolerance to the pharmacological effects of these narcotics. It is also believed that this co-administration will help to prevent the patient from becoming addicted to the narcotic. The compounds are also effective in the treatment of migraine. They can be used prophylactically or to relieve the symptoms associated with a migraine episode.

In order to exhibit these therapeutic properties, the compounds need to be administered in a quantity sufficient to inhibit the effect which the excitatory amino acids have upon the NMDA receptor complex. The dosage range at which these compounds exhibit this antagonistic effect can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.1 mg/kg/day to about 100 mg/kg/day for any of the diseases or conditions listed above. Repetitive daily administration may be desirable and will vary according to the conditions outlined above.

It has been discovered that probenecid will potentiate the therapeutic activity of the excitatory amino acid antagonists of the present invention. Thus the compounds will exhibit their therapeutic effects at lower doses and for longer periods in patients who are concurrently receiving probenecid. The mechanism by which probenecid potentiates their effects is not fully understood, however it is believed that probenecid decreases the rate at which the compounds are removed from the central nervous system as well as decreasing the rate of excretion by the kidneys. Probenecid increases the effective concentration of these compounds in both the CNS and in the systemic circulation.

Probenecid is known in the art. It is available commercially from Merck Sharp and Dohme under the tradename Benemid® as well as being available from numerous other sources. Probenecid is a uricosuric agent and is utilized in the treatment of gout. Probenecid is a renal tubular transport blocking agent and has been utilized to increase plasma levels of penicillin. The pharmacology of probenecid is described in detail in the 45th Edition of the Physicians Desk reference on page 1379. Probenecid is currently available commercially as tablets. The sodium salt of probenecid is readily water soluble and injectable dosage from can be prepared from this salt using techniques well known to those skilled in the art.

The compounds of the invention may be administered concurrently with probenecid in order to treat any of the diseases or conditions described above. The quantity of probenecid that is required to potentiate the therapeutic effects of the compounds can vary widely depending upon the particular compound being administered, the patient, and the presence of other underlying disease states within the patient, etc. Typically though, the probenecid may be administered at a dosage of from 0.5–3 g/day. Repetitive daily administration may be desirable and will vary according to the conditions outlined above. The probenecid will typically be administered from 2–4 times daily.

With the concurrent administration of probenecid, the dosage range for the excitatory amino antagonists may be adjusted lower by a factor of from 2–10. Alternatively, the compounds of Formulae I or II may be administered at the same dosage range in order to obtain an enhanced effect due to the higher therapeutic concentrations obtained.

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically an antagonistic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of Formulae Ia, Ib, IIa, or IIb, and the probenecid can be administered as two different pharmaceutical dosage forms. Alternatively, in order to increase patient convenience, the compounds and the probenecid may be compounded into a single pharmaceutical dosage form. These pharmaceutical compositions can be manufactured utilizing techniques known in the art similar to those described above. Typically an antagonistic amount of the compound of Formula I and an effective amount of probenecid will be admixed with a pharmaceutically acceptable carrier.

As used in this application:
a) the term "patient" refers to warm blooded animals such as, for example, guinea pigs, mice, rats, cats, rabbits, dogs, monkeys, chimpanzees, and humans;

b) the term "treat" refers to the ability of the compounds to either relieve, alleviate, or slow the progression of the patient's disease or prophylactically prevent its occurrence or the manifestation of its symptoms;

c) the phrase "antagonize the effects of excitatory amino acids" and the phrase "excitatory amino acid antagonist" should be referred to the ability of the compounds to inhibit or decrease the rate at which glutamate or glycine produce neurotransmission at the NMDA receptor complex, and;

d) the term "neurodegeneration" refers to a progressive death and disappearance of a population of nerve cells occurring in a manner characteristic of a particular disease state and leading to brain damage;

e) the phrase "concurrent administration" refers to administering the probenecid at an appropriate time so that it will potentiate the antagonistic effects of the compounds of Formula I, Ib, IIa, or IIb. This may means simultaneous administration or administration at appropriate but different times. Establishing such a proper dosing schedule will be readily apparent to one skilled in the art.

The compounds may also be admixed with any inert carrier and utilized in laboratory assays in order to determine the concentration of the compounds within the serum, urine, etc., of the patient as is known in the art.

Neurodegenerative diseases are typically associated with a dysfunction of NMDA receptors. Thus, the compounds of Formula I may be utilized in diagnostic procedures to aid physicians with the diagnosis of neurodegenerative diseases. The compounds may be labeled with imaging agents known in the art such as isotopic atoms and administered to a patient in order to determine whether the patient is exhibiting a decreased number of NMDA receptors and the rate at which that loss is occurring.

What is claimed is:

1. A method for antagonizing the effects of excitatory amino acids upon the NMDA receptor complex comprising administering to a patent in need thereof, an antagonistic amount of a compound of the formula:

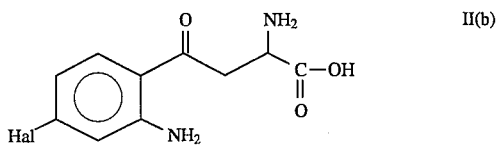

or a pharmaceutically acceptable salt thereof; in which Hal is a halogen atom.

2. A method for the treatment of epilepsy comprising administering to a patient in need thereof an anti-epileptic amount of a compound according to claim 1.

3. A method for the treatment of neurodegenerative diseases comprising administering to a patient in need thereof an effective amount of a compound according to claim 1.

4. A method for preventing ischemic/hypoxic/hypoglycemic damage to cerebral tissue comprising administering to a patient in need thereof an effective amount of a compound according to claim 1.

5. A method for the treatment of anxiety comprising administering an anxiolytic amount of a compound according to claim 1.

6. A method for producing an analgesic effect comprising administering to a patient in need thereof an analgesic amount of a compound according to claim 1.

7. A method for the treatment of migraine comprising administering an effective amount of a compound according to claim 1.

8. A pharmaceutical composition comprising a compound according to claim 1 in admixture with a pharmaceutically acceptable carrier.

9. A method for antagonizing the effects of excitatory amino acids upon the NMDA receptor complex comprising contacting the NMDA receptor of a patient in need thereof with an antagonistic amount of a compound according to claim 1.

10. A method according to claim 1 in which Hal is chlorine.

* * * * *